(12) United States Patent
Ferguson et al.

(10) Patent No.: US 9,963,319 B2
(45) Date of Patent: May 8, 2018

(54) TRI-LOCK ADJUSTABLE BUTTON LOOP

(71) Applicant: RIVERPOINT MEDICAL, LLC, Portland, OR (US)

(72) Inventors: Patrick Joseph Ferguson, Portland, OR (US); Patrick Edward Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 0 days. days.

(21) Appl. No.: 15/694,422

(22) Filed: Sep. 1, 2017

(65) Prior Publication Data

US 2017/0360437 A1 Dec. 21, 2017

Related U.S. Application Data

(63) Continuation of application No. PCT/US2017/026353, filed on Apr. 6, 2017.
(Continued)

(51) Int. Cl.
*B65H 69/04* (2006.01)
*A61B 17/06* (2006.01)
*A61B 17/04* (2006.01)
*A61B 17/00* (2006.01)
*A61F 2/08* (2006.01)

(52) U.S. Cl.
CPC ....... *B65H 69/04* (2013.01); *A61B 17/06166* (2013.01); *A61B 17/0401* (2013.01); *A61B 2017/00526* (2013.01); *A61B 2017/0404* (2013.01); *A61F 2/0811* (2013.01); *A61F 2002/0852* (2013.01)

(58) Field of Classification Search
CPC ................ B65H 69/04; A61B 17/0401; A61B 17/06166; A61F 2/0811; A61F 2002/0852
See application file for complete search history.

(56) References Cited

U.S. PATENT DOCUMENTS 5,306,301 A 4/1994 Graf et al.
6,517,578 B2 2/2003 Hein
(Continued)

OTHER PUBLICATIONS

Patent Cooperation Treaty (PCT), International Searching Authority, Application No. PCT/US17/26353, International Searth Report and Written Opinion, dated Aug. 1, 2017.
(Continued)

*Primary Examiner* — Shaun R Hurley
(74) *Attorney, Agent, or Firm* — Timothy E. Siegel Patent Law, PLLC; Timothy E. Siegel

(57) ABSTRACT

A suture assembly, including a button having two apertures and a suture defining a lumen and forming a double loop, formed by a double trap having a first end and a second end, opposed to the button. A first portion of the suture is threaded through the trap from the first end to the second end, and a second portion of the suture is threaded through the trap from the second end to the first end. The assembly further defines a first single trap, in which the first portion of the suture is threaded through the lumen between the second end and the button. Also defined by the assembly is a third trap, in which the second portion of the suture is threaded through the lumen between the first end and the button. Finally, the double loop is threaded through the two apertures of the button.

6 Claims, 8 Drawing Sheets

Related U.S. Application Data

(60) Provisional application No. 62/319,115, filed on Apr. 6, 2016.

(56) References Cited

U.S. PATENT DOCUMENTS

| | | | |
|---|---|---|---|
| 8,088,130 | B2 | 1/2012 | Kaiser et al. |
| 8,118,836 | B2 | 2/2012 | Denham et al. |
| 8,460,379 | B2 | 6/2013 | Albertorio et al. |
| 8,672,969 | B2 * | 3/2014 | Stone ............ A61B 17/0401 606/213 |
| 8,801,783 | B2 * | 8/2014 | Stone ............ A61B 17/0401 623/13.13 |
| 8,936,621 | B2 * | 1/2015 | Denham ........ A61B 17/0401 606/228 |
| 9,204,960 | B2 | 12/2015 | Albertorio et al. |
| 9,216,078 | B2 | 12/2015 | Conner et al. |
| 9,333,069 | B2 | 5/2016 | Denham |
| 2007/0233151 | A1 | 10/2007 | Chudik |
| 2008/0177302 | A1 * | 7/2008 | Shurnas ......... A61B 17/0401 606/228 |
| 2008/0312689 | A1 | 12/2008 | Denham et al. |
| 2009/0312776 | A1 | 12/2009 | Kaiser et al. |
| 2009/0318961 | A1 | 12/2009 | Stone et al. |
| 2010/0268273 | A1 | 10/2010 | Albertorio et al. |
| 2011/0087280 | A1 * | 4/2011 | Albertorio ...... A61B 17/0401 606/232 |
| 2013/0317544 | A1 | 11/2013 | Ferguson et al. |
| 2015/0173739 | A1 | 6/2015 | Rodriguez et al. |
| 2016/0128684 | A1 | 5/2016 | Stone et al. |
| 2017/0202553 | A1 * | 7/2017 | Ferguson ....... A61B 17/06166 |

OTHER PUBLICATIONS

Boyle, M.J. et al., ACL TightRope Scientific Update, Arthrex, Inc., LA1-00021-EN_B, pp. 1-2, 2016.

Watson, John, "Endobutton CL Ultra fixed-length cortical suspension device vs. adjustable-loop fixation designs: Review of mechanical data", Bone & Joint Science, vol. 4, No. 4, pp. 1-9, Oct. 2004.

FPO IP Research & Communities, downloaded May 24, 2016.

FPO IP Research & Communities, downloaded May 25, 2016.

"Advanced ACL/PCL Graft Fixation Options . . . Simplified", TightRope Implant, Arthrex, Inc., LB1-0179-EN-B, pp. 1-12, 2016.

McCarty, Eric, M.D., "ACL Reconstruction" Biomet Sports Medicine, Mar. 2009.

* cited by examiner

TRI-LOCK ADJUSTABLE BUTTON LOOP

RELATED APPLICATIONS

This application is a continuation of International Application number PCT/US17/26353, filed on Apr. 6, 2017, which claims the benefit of priority to U.S. Provisional Application No. 62/319,115, filed Apr. 6, 2016, which are incorporated herein by reference as if fully set forth herein.

BACKGROUND

Continuous loop suture and button assemblies are commonly used during orthopedic surgery for bone-tendon-bone, single-bundle soft tissue, and double bundle soft tissue fixation, such as during cruciate reconstruction. For example, during anterior cruciate ligament (ACL) reconstruction, a bone-tendon-bone graft is commonly positioned within both the femur and tibia bones. These grafts are often secured to a continuous loop/button assembly, which are in turn anchored to a bone. One example of a loop/button assembly is disclosed in U.S. Pat. No. 6,533,802 to Bojarski et al. ("Bojarksi"). Bojarski references a few different general methods of attaching a button to a continuous loop: (a) start with a closed loop suture and then capture the button by threading loop sections through openings in the button or wrapping the loop sections around channels/arms of the button (e.g., Bojarksi FIG. 12), (b) start with a thread having a leading end and utilize an automated winding machine to continuously wrap the leading end through apertures in the button to form a closed loop, such as disclosed in WO99/47079 to Bryant ("Bryant"), or (c) provide a suture with two open ends, thread and/or wrap the suture to an anchor button and then tie the open ends together, such as disclosed in U.S. Pat. No. 5,769,894 to Ferragamo ("Ferragamo"). The above described methods of making continuous loop and button assemblies result in products that are susceptible to breaking over time due to mechanical stress.

Additionally, U.S. Pat. No. 9,357,990 describes an assembly having a fixed sized loop attached to a button. This has provided a helpful advance in the art.

U.S. Pat. No. 6,517,578 discloses a device similar to those described in the references discussed above, except for that the suture loop that is threaded through the buttonholes has a variable size. To achieve this result a double trap is used with two suture lengths crossing each other inside a lumen in another length of the same suture. This adjustability permits the surgeon using the device to adjust it prior to use, and also to adjust the loop size during surgery. There is an advantage in not having to keep many different sizes of suture loop-button constructs on hand for surgeries on patients with differing bone thicknesses. Unfortunately, during use, the loop tends to expand, due to slippage in the double trap, leading to problems with the ligament implantation. Efforts to create a suture having less slippage by expanding the length of the double trap have met with issues in the construction of the construct.

SUMMARY

In a first, separate aspect, the present invention may take the form of a suture assembly, including a button having two apertures and a suture defining a lumen and forming a double loop, formed by a double trap having a first end and a second end, opposed to the button. A first portion of the suture is threaded through the trap from the first end to the second end, and a second portion of the suture is threaded through the trap from the second end to the first end. The assembly further defines a first single trap, in which the first portion of the suture is threaded through the lumen between the second end and the button. Also defined by the assembly is a third trap, in which the second portion of the suture is threaded through the lumen between the first end and the button. Finally, the double loop is threaded through the two apertures of the button.

In a second separate aspect, the present invention may take the form of a method of making a suture assembly that utilizes a length of suture having a first and second end and defining a lumen and a button having at least a first and second aperture. The first end is drawn through the first aperture and through the second aperture and introduced into the lumen at a first point and drawn out of the lumen at a second point. The second end is drawn through the second aperture and through the first aperture and introduced into the lumen at the second point and drawn out of the lumen at the first point, thereby creating a double trap region containing two suture lengths, crossing each other. Then, the first end is introduced into the lumen at a third point, in between the second point and the button, and drawn out of the lumen at a fourth point, closer to the button than the third point, thereby creating a second trap region. Also, the second end is drawn into the lumen at a fifth point, in between first point and the button and drawn out of the lumen at a sixth point, closer to the button than the fifth point, thereby creating a third trap region.

In a third separate aspect, the present invention may take the form of a method of performing a tendon replacement, of a tendon connecting a first bone and a second bone, in an animal body utilizing a suture assembly that includes the following construction. A button has two apertures and a suture defines a lumen and forms a double loop, formed by a double trap having a first end and a second end, formed in a double trap portion of the suture, opposed to the button. A first portion of the suture is threaded through the trap region lumen from the first end to the second end, and a second portion of the suture is threaded through the trap region lumen from the second end to the first end. The suture assembly further defines a first single trap, in which the first portion of the suture, after emerging from the second end of the double trap, is threaded through the lumen between the second end and the button and a third trap, in which the second portion of the suture, after emerging from the first end of the double trap, is threaded through the lumen between the first end and the button. Also, the double loop is threaded through the apertures of the button. Finally, the suture has two suture ends that are threaded through the button apertures and accessible on a side of the button opposed to the double loop. In the method, a drill hole is drilled sequentially through the two bones. Also, a length of tendon tissue is draped over the loop and the button is passed through the drill hole through the first bone and the second bone, and orienting the button to sit on a surface of the second bone and the suture ends extend outwardly through the drill hole of the second bone on the side on which the button is situated. Finally, the suture ends are pulled to constrict the double loop.

DETAILED DESCRIPTION OF THE PREFERRED EMBODIMENTS

Figure 1:
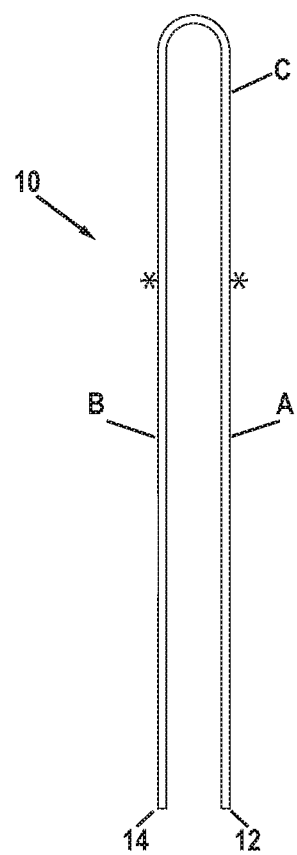
FIG. 1 is an illustration of a suture showing the definition of three regions

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
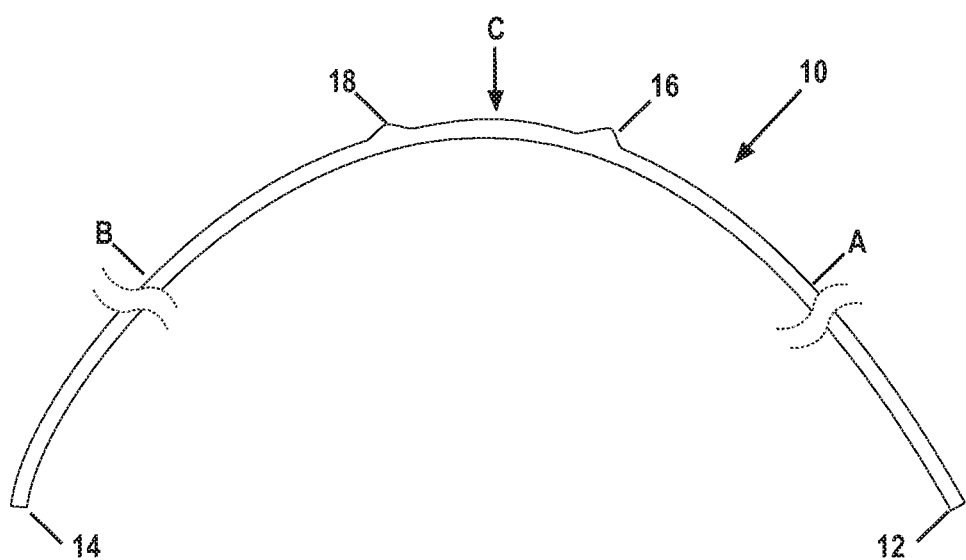
FIG. 2 is an illustration of the suture of FIG. 1, with two places fluffed to facilitate introduction of a suture portion into a lumen defined interior to the suture.

FIG. 1 shows a length of fiber or suture 10, bent in a U-shape and having a first end 12 and an opposed second end 14. Also, three thirds of the suture 10 are indicated, a first third A, an opposing third B, and a central third C. In a preferred embodiment, suture 10 is a braid that defines an inner lumen. As shown in FIG. 2, the suture 10 is preferably fluffed at the entry point 16 and exit point 18 points to make it easier for a lacing tool 22 (FIG. 3) to be inserted through the trap section 20. One end of the lacing tool 22 can include a handle to allow a user to position, guide, push, and pull the tool. The lacing tool 22 also includes a main body that is preferably substantially linear and having a diameter, or cross-section, small enough to thread through the suture 10. The end of the lacing tool 22 opposite of the handle can include a hinged barb 24 to allow for coupling to the suture 10. The hinge allows the barb 24 to have a lower profile when traversing through the inside of suture 10 while minimizing the chance of snags. Other means for coupling to the suture 10 are readily contemplated and can nonexclusively include one or more barbs (hinged or unhinged) hooks, clamps (such that can be opened and closed by the handle) and the like, for example. Said means for coupling preferably should not prevent or hinder the lacing tool 22 from being pushed into or pulled out of the inside of the suture 10. In a preferred embodiment fiber or suture 10 is made of ultra-high molecular weight polyethylene (UHM-WPE).

Figure 3:
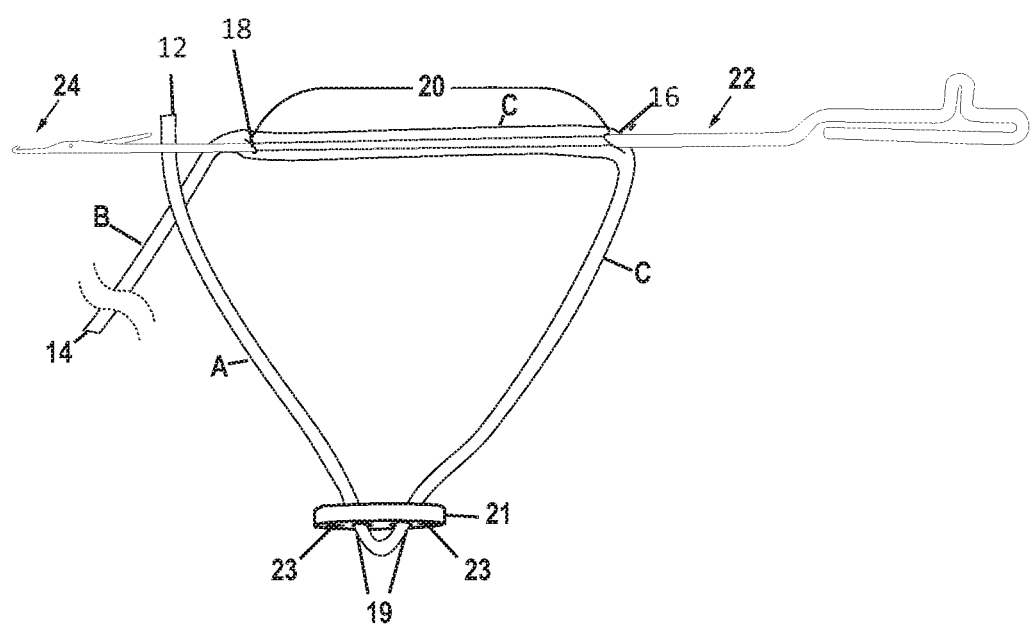
FIG. 3 is an illustration of the suture of FIG. 1, now engaged to a button and with a lacing tool introduced through a section of the suture and in the process of engaging and end of the suture.

As depicted in FIG. 3, suture 10 has been threaded through two interior apertures 19 of a button 21, which also has two exterior apertures 23. A trap section 20 is defined, between sections 16 and 18, and the barb 24 of the lacing tool 22 is pushed into the lumen of the suture 10 at the fluffed entry point 16. The barb 24 is pushed through the inside of the trap section 20 and guided outward through the fluffed exit point 18. Suture end 12 is then grasped by the barb 24 and drawn through exit point 18 and out through point 16. The result of this operation (not shown) is that end 12 extends through trap section 20, exiting at point 16, and forming a loop 26 (FIG. 4).

Figure 4:
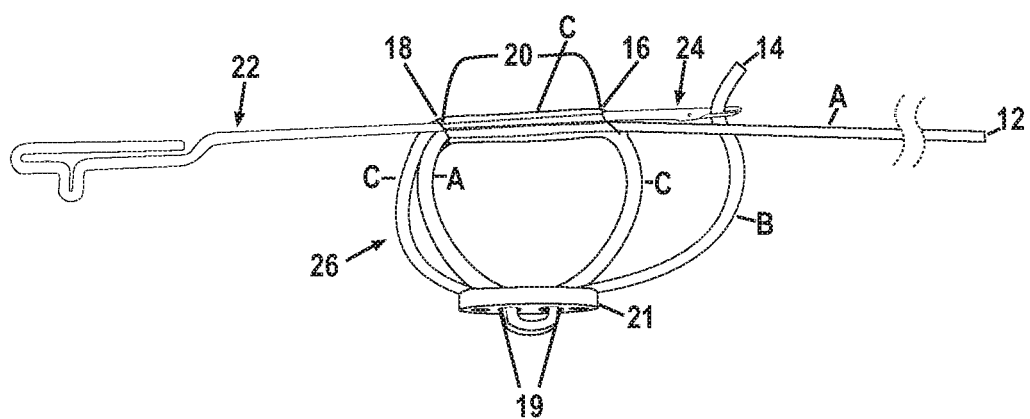
FIG. 4 is an illustration of the elements of FIG. 3, now at a further stage of construction of a suture assembly.
Figure 5:
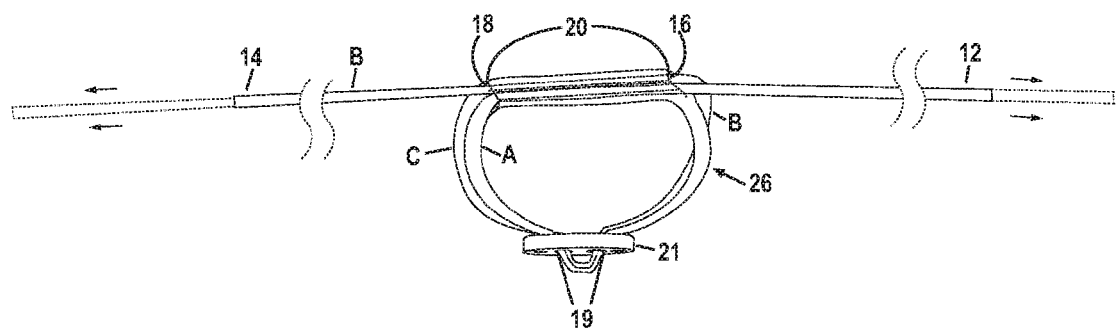
FIG. 5 is an illustration of the elements of FIG. 4, now at a further stage of construction of a suture assembly.

Referring to FIG. 4, second end 14 is threaded through apertures 19, seized by barb 24 and drawn back through trap section 20, entering through second point 18 and exiting through first point 16. The result is shown in FIG. 5, having a double loop 26, and the ends (12 and 14) extending out of loop 26 in either direction. Trap section 20 is now a double trap, having portion A of suture 10 going through trap section 20 from second point 18 to first point 16 and portion B of suture 10 going through trap section 20 in the opposite direction.

Figure 6:
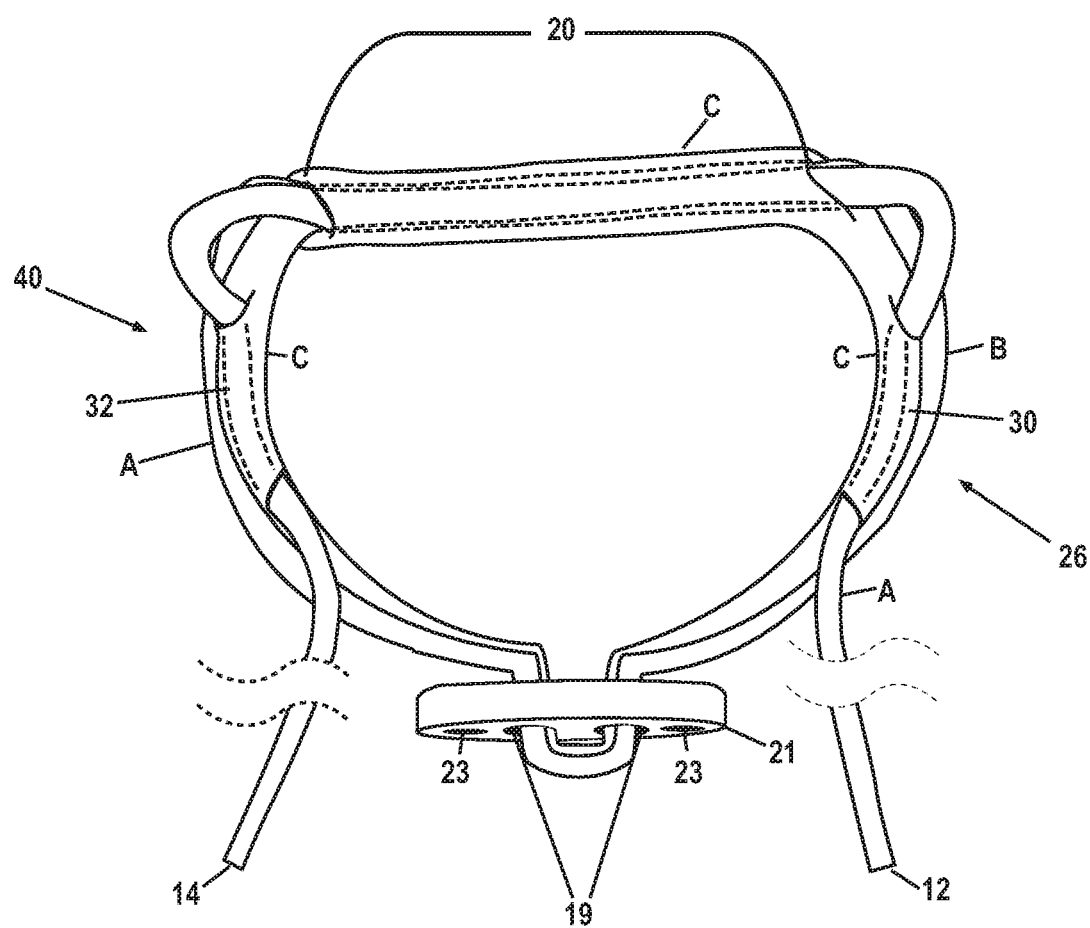
FIG. 6 is an illustration of the elements of FIG. 5, now at a further stage of construction of a suture assembly.
Figure 7:
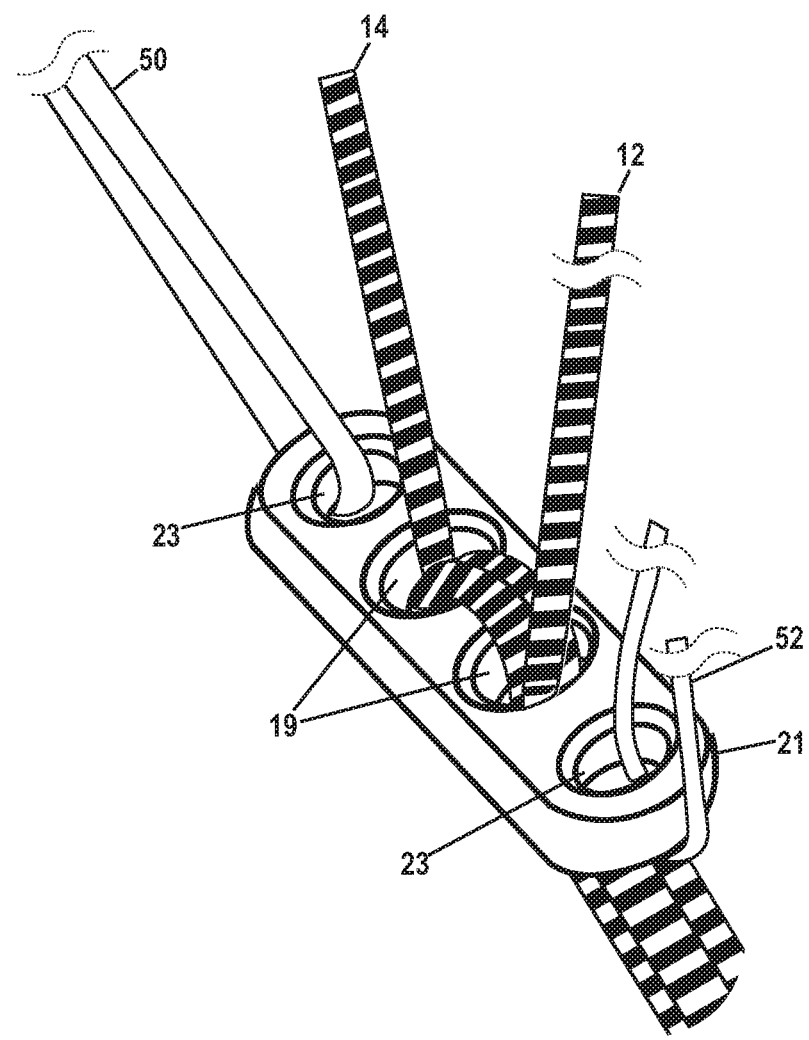
FIG. 7 is an illustration of a top view of a portion of a finished suture assembly according to the present invention.

Referring to FIG. 6, end tail 12 is pulled into and then out of a portion of central third C of suture 10, between the double trap of trap section 20 and the button 21, creating an additional trap 30. A parallel operation is performed, pulling end tail 14 into and then out of a portion of central third C of suture 10, between the double trap of trap section 20 and the button 21, creating yet another trap 32, and a substantially finished suture and button assembly 40. FIG. 7 shows the top portion of assembly 40, with the suture ends 12 and 14 extending through apertures 19, and with positioning and/or connecting tension elements 50 and 52 looped through apertures 23. In a preferred embodiment suture 10 is banded, as shown in FIG. 7.

The three traps 20, 30 and 32 collectively create a greater total amount of resistance to slipping in assembly 40. Slipping can cause an undesirable expansion of the loop 26, after implantation. Accordingly, resistance to slipping, in prevent this undesirable widening, is an important factor in assembly 40 performance. Assembly 40 permits adjustment by cinching of double loop 26, as the assembly 40 is being implanted by a surgeon, and then greatly resists any widening of double loop 26, even during an extensive period of use subsequent to implantation. In an alternative preferred embodiment, ends 12 and 14 are each fed through one of the apertures 19, to provide further resistance to slippage. This design permits 3 mm or less of loop widening through use, after implantation. This is a generally acceptable amount that will not harm a patient. Loop 26 is typically between 12 and 60 mm in circumference.

Non-limiting examples of buttons that can be used with the teachings herein, include the anchor of the XO BUTTON® commercially available by CONMED®/LINVATEC® and suitable buttons disclosed in U.S. Pat. No. 6,533,802 to Bojarski et al., and U.S. Pat. No. 5,306,301 to Graf et al., Thus the buttons used in the teachings herein can be a variety of shapes, non-exclusively including oval, racetrack, circular, square, rectangular, and can have 1, 2, 3, 4, 5, 6, or more apertures for allowing the continuous loop or additional sutures to be threaded through. Apertures can be circular, ovular, square, rectangular, and the like as well. Additionally the button can include cantilevered arms defining channels, if so desired. Any of the above buttons are suitable in that they can couple to the continuous loop in a manner that an intact button cannot be detached from the loop without opening or breaking the loop.

Buttons are advantageously made from any suitable surgically implantable biocompatible material, non-exclusively including metal, including surgical steel and titanium, or thermoplastics, for example. Alternatively, buttons can be made of a biocompatible thermoplastic as well, for example. In one embodiment the button 21 has a length of between 11 and 12 mm and a width of between 3 and 6 mm. The trap section 20 has a length of between 15 and 18 mm. If loosely pulled the length of double loop 26 from button to the furthest point, in one embodiment is 60 mm. In one embodiment the double loop 26 is stretched beyond 60 mm, from button to furthest point, to set the traps 20, 30 and 32.

Figure 8:
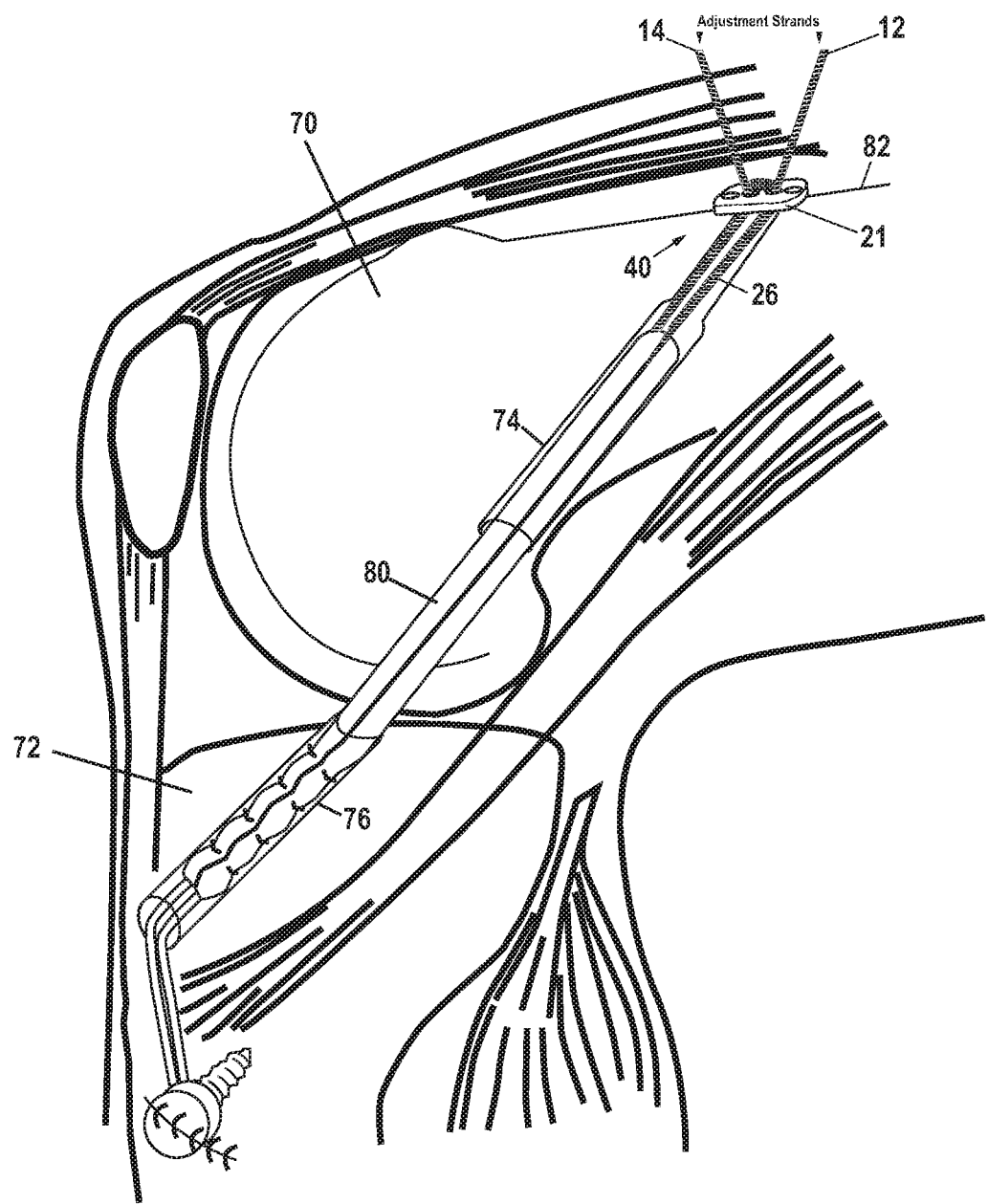
FIG. 8 is an illustration of the suture assembly of FIG. 7 in use in the repair of a knee.

Referring now to FIG. 8, In most typical use, the above described assembly is used in the replacement of the anterior cruciform ligament, binding the femur 70 to the tibia 72. To achieve this end, roughly aligned holes 74 and 76, are drilled through these two bones 70, 72 and a graft ligament 80 is draped over the double loop 26. The button 21 is passed from the tibia through the two aligned holes 74, 76 to emerge at the top of the femur, where it is seated on the cortex 82, with the loop 26 extending into the femur hole and the graft ligament 80 extending through the aligned holes 74, 76, from the femur hole 74 to the roughly aligned tibia hole 76. At this point, the suture ends 12, 14 are available to be pulled, on the femur end of the aligned holes, and this is done to constrict the double loop and pull the graft ligament into a preferred position for forming attachment to the tunnel walls and binding together the femur 70 and the tibia 72 of the patient. It may also be noted that the loop size may be adjusted prior to surgery, so that a smaller number of sizes can be stocked.

The invention claimed is:

1. A method of making a suture assembly, comprising:
   (a) providing a length of suture having a first and second end and defining a lumen and a button having at least a first and second aperture;
   (b) drawing said first end through said first aperture and through said second aperture
   (c) introducing said first end into said lumen at a first point and drawing said first end out of said lumen at a second point;
   (d) drawing said second end through said second aperture and through said first aperture;
   (e) introducing said second end into said lumen at said second point and drawing said second end out of said lumen at said first point thereby creating a double trap region containing two suture lengths, crossing each other;
   (f) introducing said first end into said lumen at a third point, in between said second point and said button and drawing said first end out of said lumen at a fourth point, closer to said button than said third point, thereby creating a second trap region;
   (g) introducing said second end into said lumen at a fifth point, in between first point and said button and drawing said second end out of said lumen at a sixth point, closer to said button than said fifth point, thereby creating a third trap region.

2. The method of claim 1, wherein said button has additional apertures that are free of sutures and available to be threaded to an additional suture during surgery.

3. The method of claim 2, wherein said additional apertures are arranged symmetrically about said two apertures.

4. The method of claim 1, wherein said suture is made of ultra-high molecular weight polyethylene.

5. The method of claim 1, wherein said button is rectangular with rounded ends.

6. The method of claim 1, wherein said first and second ends of said length of suture are threaded through said apertures and accessible on a side of said button opposed to said double loop.

* * * * *